(12) United States Patent
Roy et al.

(10) Patent No.: US 7,377,276 B2
(45) Date of Patent: May 27, 2008

(54) AUTOMATED INHALATION TOXICOLOGY EXPOSURE SYSTEM AND METHOD

(75) Inventors: Chad J. Roy, Keedysville, MD (US); Justin M. Hartings, Clarksburg, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 965 days.

(21) Appl. No.: 10/166,228

(22) Filed: May 29, 2002

(65) Prior Publication Data
US 2003/0055354 A1    Mar. 20, 2003

Related U.S. Application Data

(63) Continuation-in-part of application No. 09/919,741, filed on Jul. 31, 2001, now Pat. No. 6,904,912.
(60) Provisional application No. 60/267,233, filed on Jan. 31, 2001.

(51) Int. Cl.
    *A61M 11/00*      (2006.01)
    *A61M 15/00*      (2006.01)
    *A61M 16/00*      (2006.01)
    *A01K 1/03*      (2006.01)
(52) U.S. Cl. ............................ 128/203.14; 128/200.14; 119/420
(58) Field of Classification Search ................ 600/529; 128/202.12, 203.12; 419/15, 17
See application file for complete search history.

(56) References Cited

U.S. PATENT DOCUMENTS 3,548,840 A    12/1970    Baumgartner ................ 131/171

(Continued)

FOREIGN PATENT DOCUMENTS

EP      0 610 171 B1      8/1994

(Continued)

OTHER PUBLICATIONS

EMKA Technologies, "*Software and Hardware for Pulmonary Applications*", 1 pg.

(Continued)

*Primary Examiner*—Robert L. Nasser
(74) *Attorney, Agent, or Firm*—Elizabeth Arwine

(57) ABSTRACT

In one embodiment, a method includes but is not limited to: conditioning an inhalent environment; exposing a first organism to the inhalent environment for a first-organism duration of time; and exposing a second organism to the inhalent environment for a second-organism duration of time. In one embodiment, a method includes but is not limited to: conditioning an inhalent environment; exposing a first organism to the inhalent environment until a calculated first-organism delivered dosage meets or exceeds a predefined first-organism target dosage; and exposing a second organism to the inhalent environment until a calculated second-organism delivered dosage meets or exceeds a predefined second-organism target dosage. In one embodiment, a method includes but is not limited to: detecting a first organism via a first-organism biochip device implanted in the first organism; and controlling a first-organism dosage in response to the first-organism biochip device. In addition to the foregoing, other method embodiments are described in the claims, drawings, and text forming a part of the present application. In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer. In one embodiment, a system includes but is not limited to: an inhalent manifold; a first independently-controllable exposure unit coupled to said inhalent manifold; a second independently-controllable exposure unit coupled to said inhalent manifold; and an exposure control system operably coupled to either or both said first independently-controllable exposure unit and said second independently-controllable exposure unit.

103 Claims, 4 Drawing Sheets

U.S. PATENT DOCUMENTS

| | | | |
|---|---|---|---|
| 4,201,154 A | 5/1980 | Gowrie | |
| 4,216,741 A | 8/1980 | Moss | |
| D262,320 S | 12/1981 | Monö | |
| 4,305,347 A | 12/1981 | Hemenway et al. | |
| 4,347,712 A * | 9/1982 | Benton et al. | 62/175 |
| 4,348,985 A | 9/1982 | Leong | |
| 4,463,706 A | 8/1984 | Meister et al. | 119/51 R |
| 4,510,929 A | 4/1985 | Bordoni et al. | |
| 4,520,808 A | 6/1985 | LaBauve | |
| 4,532,892 A | 8/1985 | Kuzara | 119/51 R |
| 4,570,630 A | 2/1986 | Elliott et al. | |
| 4,598,704 A | 7/1986 | Bordoni et al. | |
| 4,674,490 A | 6/1987 | Frankel et al. | |
| 4,703,753 A | 11/1987 | Bordoni et al. | |
| 4,721,060 A | 1/1988 | Cannon et al. | |
| 4,787,384 A | 11/1988 | Campbell et al. | 128/330 |
| 4,860,741 A | 8/1989 | Bernstein et al. | 128/204.18 |
| 4,940,051 A | 7/1990 | Lankinen | |
| 5,025,619 A | 6/1991 | Cannon | |
| 5,082,471 A | 1/1992 | Athayde et al. | |
| 5,099,792 A | 3/1992 | Cannon et al. | 119/15 |
| 5,109,797 A | 5/1992 | Briant et al. | |
| 5,156,776 A | 10/1992 | Loedding et al. | |
| 5,297,502 A | 3/1994 | Jaeger | |
| 5,320,108 A | 6/1994 | Cloutier | |
| 5,379,777 A | 1/1995 | Lomask | 128/716 |
| 5,467,764 A | 11/1995 | Gamow | |
| 5,622,164 A | 4/1997 | Kilis et al. | |
| 5,626,130 A | 5/1997 | Vincent et al. | 128/203.12 |
| 5,887,586 A | 3/1999 | Dahlbäck et al. | 128/204.22 |
| 5,896,829 A | 4/1999 | Rothenberg et al. | |
| 5,954,049 A | 9/1999 | Foley et al. | |
| 6,016,803 A | 1/2000 | Volberg et al. | |
| 6,131,571 A | 10/2000 | Lampotang et al. | |
| 6,138,668 A | 10/2000 | Patton et al. | |
| 6,192,876 B1 | 2/2001 | Denyer et al. | |
| 6,352,076 B1 | 3/2002 | French | |
| 6,380,859 B1 | 4/2002 | Brownlee | |
| 6,565,624 B2 | 5/2003 | Kutt et al. | |
| 6,584,971 B1 | 7/2003 | Denyer | |
| 6,694,977 B1 | 2/2004 | Federowicz et al. | |

FOREIGN PATENT DOCUMENTS

| | | |
|---|---|---|
| EP | 0 667 168 A1 | 8/1995 |
| WO | WO 91/06832 | 5/1991 |
| WO | WO 96/13294 A1 | 5/1996 |

OTHER PUBLICATIONS

EMKA Technologies, "*Develops, Manufactures and sells hardware and Software for Studies in Physiology, Pharmacology and Toxicology*", 11 pgs.

TSE Technical and Scientific Equipment GmbH, "*TSE Exposys, Planning, Control and Analysis of Inhalation Experiments*", 11 pgs.

RCC Ltd. Pharmaceutical Industry, "*Inhalation Toxicology*", 2 pgs.

Huntingdon Life Sciences, "*Inhalation Toxicology, for Pharmaceutical Development and Chemical Safety*", 4 pgs.

Kenny, T.J. et al., "*Whole Body Exposure System for Administering Nitric Oxide (KINOX®) by Inhalation to Neonate Rats*," Huntingdon Life Sciences, 4 pgs.

Battelle, "*NORES® Nose-Only Rodent Inhalation Exposure System*", 2 pgs.

ITR Laboratories Canada Inc., "*Inhalation Toxicology*", 2 pgs.

TSE Technical and Scientific Equipment GmbH, "*TSE OptoPan, For Aerosol assessment during Inhalation Studies*", 6 pgs.

TSE Technical and Scientific Equipment GmbH, "*TSE Inhalation Systems, Aerosol Generation, Process Control and Analysis*", 17 pgs.

English abstract for EP 0610171 B1.

* cited by examiner

AUTOMATED INHALATION TOXICOLOGY EXPOSURE SYSTEM AND METHOD

CROSS-REFERENCE TO RELATED APPLICATION

The present patent application is a continuation-in-part of and hereby incorporated by reference in its entirety, U.S. patent application Ser. No. 09/919,741, entitled Automated Inhalation Toxicology Exposure System, filed Jul. 31, 2001, now U.S. Pat. No. 6,904,912 B2, and naming Chad J. Roy and Justin M. Hartings as inventors, which claims the benefit of U.S. Provisional Patent Application No. 60/267,233, filed Jan. 31, 2001, entitled Automated Inhalation Toxicology Exposure System, and naming Chad J. Roy and Justin M. Hartings as inventors; the present patent application also hereby incorporates by reference in its entirety any subject matter which was itself incorporated by reference into the previously-referenced U.S. patent application Ser. No. 09/919,741, entitled Automated Inhalation Toxicology Exposure System, such as U.S. Provisional Patent Application No. 60/267,233.

STATEMENT REGARDING FEDERALLY SPONSORED RESEARCH OR DEVELOPMENT

This invention was made with government support. The government has certain rights in this invention.

BACKGROUND OF THE INVENTION

1. Field of the Invention

The present application relates, in general, to multi-animal inhalation exposure systems.

2. Description of the Related Art

Multi-animal inhalation exposure studies are generally performed using multi-animal inhalant systems. In multi-animal inhalation exposure studies, two or more animals are usually exposed to an organic or inorganic inhalant within the confined space of an inhalant chamber forming part of an inhalant system.

In the related art, a multi-animal inhalant system is typically one that provides mechanisms for exposing two or more animals to an inhalant. The inventors named herein ("inventors") have noticed several deficiencies and/or unmet needs associated with related-art multi-animal inhalant systems, a few of which will now be set forth (other related-art deficiencies and/or unmet needs will become apparent in the detailed description below).

The inventors have discovered that it would be advantageous for a multi-animal inhalant system to be able to condition an inhalent environment prior to exposing animals to the inhalent environment. The inventors have discovered that related-art multi-animal inhalant systems do not tend to provide for the conditioning of an inhalent environment prior to exposing the animals to the inhalent environment. The inventors have thus recognized that a need exists in the art for a multi-animal inhalent system that provides the ability to condition an inhalent environment prior to exposing the animals to the inhalent environment.

The inventors have discovered that it would be advantageous for a multi-animal inhalant system to be able to provide for differing exposure durations during which animals are exposed to the same inhalent environment. The inventors have discovered that related-art multi-animal inhalent systems do not tend to provide for differing exposure durations during which animals are exposed to the same inhalent environment. The inventors have thus recognized that a need exists in the art for a multi-animal inhalent system that provides for differing exposure durations during which animals are exposed to the same inhalent environment.

The inventors have discovered that it would be advantageous for a multi-animal inhalent system to be able to provide control such that the exposure duration for each animal can be determined based on respiratory volume measurements. The inventors have discovered that related-art multi-animal inhalent systems do not tend to provide control such that the exposure duration for each animal can be determined based on respiratory volume measurements. The inventors have thus recognized that a need exists in the art for a multi-animal inhalent system that provides control such that the exposure duration for each animal can be determined based on respiratory volume measurements.

The inventors have discovered that it would be advantageous for a multi-animal inhalent system to be able to automatically control inhalent dose delivery and recording functions on an identified-animal basis. The inventors have discovered that related-art multi-animal inhalent systems do not automatically control inhalent dose delivery and recording functions on an identified-animal basis. The inventors have thus recognized that a need exists in the art for a multi-animal inhalent system that automatically controls inhalent dose delivery and recording functions on an identified-animal basis.

The foregoing-described inventor discoveries constitute at least a part of the inventive content herein.

BRIEF SUMMARY OF THE INVENTION

In one embodiment, a method includes but is not limited to: conditioning an inhalent environment; exposing a first organism to the inhalent environment for a first-organism duration of time; and exposing a second organism to the inhalent environment for a second-organism duration of time. In another method embodiment, said conditioning an inhalent environment is characterized by: introducing an inhalent into an inhalent manifold. In another method embodiment, said introducing an inhalent into an inhalent manifold is characterized by: introducing the inhalent into an inhalent intake plenum operably coupled with an inner manifold. In another method embodiment, said conditioning an inhalent environment is characterized by: monitoring at least one environmental condition selected from an environmental-condition group including temperature, relative humidity, pressure, and inhalent concentration. In another method embodiment, said conditioning an inhalent environment is characterized by: adjusting at least one environmental condition selected from an environmental-condition group including temperature, relative humidity, pressure, and inhalent concentration. In another method embodiment, said exposing a first organism to the inhalent environment for a first-organism duration of time is characterized by: coupling the inhalent environment to a first apertured connector, containing at least a part of the first organism, for the first-organism duration of time. In another method embodiment, said coupling the inhalent environment to a first apertured connector, containing at least a part of the first organism, for the first-organism duration of time is characterized by: starting the first-organism duration of time upon an initial coupling of the inhalent environment to the first apertured connector containing the at least a part of the first organism; and terminating the first-organism duration of time when a calculated first-organism delivered dosage meets or exceeds a predefined first-organism target dosage. In another method embodiment, said terminating the first-organism duration of time when a calculated first-organism delivered dosage meets or exceeds a predefined first-organism target dosage is characterized by: detecting the first organism via a first-organism biochip device implanted in the first organism; and recalling the predefined first-organism target dosage in response to the first-organism biochip device. In another method embodiment, said terminating the first-organism duration of time when a calculated first-organism delivered dosage meets or exceeds a predefined first-organism target dosage is characterized by: measuring a volume respirated by the first organism; calculating the first-organism delivered dosage in response to the volume. In another method embodiment, said measuring a volume respirated by the first organism is characterized by: measuring a volume of an animal restraint cartridge associated with a first-organism biochip device. In another method embodiment, said measuring a volume of an animal restraint cartridge associated with a first-organism biochip device is characterized by: measuring a flow between an interior of the animal restraint cartridge and an exterior of the animal restraint cartridge. In another method embodiment, said coupling the inhalent environment to a first apertured connector, containing at least a part of the first organism, for the first-organism duration of time is characterized by: opening a valve between the inhalent environment and the first apertured connector at a first-organism beginning time; and closing the valve between the inhalent environment and the first apertured connector at a first-organism ending time. In another method embodiment, said coupling the inhalent environment to a first apertured connector, containing at least a part of the first organism, for the first-organism duration of time is characterized by: closing a valve between a clean-air environment and the first apertured connector at a first-organism beginning time; and opening a valve between the clean-air environment and the first apertured connector at a first-organism ending time. In another method embodiment, said exposing a second organism to the inhalent environment for a second-organism duration of time is characterized by: coupling the inhalent environment to a second apertured connector containing at least a part of the second organism for the second-organism duration of time. In another method embodiment, said coupling the inhalent environment to a second apertured connector containing at least a part of the second organism for the second-organism duration of time is characterized by: starting the second-organism duration of time upon an initial coupling of the inhalent environment to the second apertured connector containing the at least a part of the second organism; and terminating the second-organism duration of time when a calculated second-organism delivered dosage meets or exceeds a predefined second-organism target dosage. In another method embodiment, said terminating the second-organism duration of time when a calculated second-organism delivered dosage meets or exceeds a predefined second-organism target dosage is characterized by: detecting the second organism via a second-organism biochip device implanted in the second organism; and recalling the predefined second-organism target dosage in response to the second-organism biochip device. In another method embodiment, said terminating the second-organism duration of time when a calculated second-organism delivered dosage meets or exceeds a predefined second-organism target dosage is characterized by: measuring a volume respirated by the second organism; and calculating the delivered dosage in response to the volume. In another method embodiment, said measuring a volume respirated by the second organism is characterized by: measuring a volume of an animal restraint cartridge associated with a second-organism biochip device. In another method embodiment, said measuring a volume of an animal restraint cartridge associated with a second-organism biochip device is characterized by: measuring a flow between an interior of the animal restraint cartridge and an exterior of the animal restraint cartridge. In another method embodiment, said coupling the inhalent environment to a second apertured connector containing at least a part of the second organism for the second-organism duration of time is characterized by: opening a valve between the inhalent environment and the second apertured connector at a second-organism beginning time; and closing the valve between the inhalent environment and the second apertured connector at a second-organism ending time. In another method embodiment, said coupling the inhalent environment to a second apertured connector containing at least a part of the second organism for the second-organism duration of time is characterized by: closing a valve between a clean-air environment and the second apertured connector at a second-organism beginning time; and opening the valve between the clean-air environment and the second apertured connector at a second-organism ending time. In another method embodiment, the method is further characterized by performing an inhalent or exposure study, wherein said performing the inhalent or exposure study is characterized by said conditioning, said exposing a first organism, and said exposing a second organism. In addition to the foregoing, other method embodiments are described in the claims, drawings, and text forming a part of the present application.

In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer.

In one embodiment, a method includes but is not limited to: conditioning an inhalent environment; exposing a first organism to the inhalent environment until a calculated first-organism delivered dosage meets or exceeds a predefined first-organism target dosage; and exposing a second organism to the inhalent environment until a calculated second-organism delivered dosage meets or exceeds a predefined second-organism target dosage. In another method embodiment, said conditioning an inhalent environment is characterized by: introducing an inhalent into an inhalent manifold. In another method embodiment, said introducing an inhalent into an inhalent manifold is characterized by: introducing the inhalent into an inhalent intake plenum operably coupled with an inner manifold. In another method embodiment, said conditioning an inhalent environment is characterized by: monitoring at least one environmental condition selected from an environmental-condition group including temperature, relative humidity, pressure, and inhalent concentration. In another method embodiment, said conditioning an inhalent environment is characterized by: adjusting at least one environmental condition selected from an environmental-condition group including temperature, relative humidity, pressure, and inhalent concentration. In another method embodiment, said exposing a first organism to the inhalent environment until a calculated first-organism delivered dosage meets or exceeds a predefined first-organism target dosage is characterized by: detecting the first organism via a first-organism biochip device implanted in the first organism; and recalling the predefined first-organism target dosage in response to the first-organism biochip device. In another method embodiment, said exposing a first organism to the inhalent environment until a calculated first-organism delivered dosage meets or exceeds a predefined first-organism target dosage is characterized by: measuring a volume respirated by the first organism; calculating the first-organism delivered dosage in response to the volume. In another method embodiment, said measuring a volume respirated by the first organism is characterized by: measuring a volume of an animal restraint cartridge associated with a first-organism biochip device. In another method embodiment, said measuring a volume of an animal restraint cartridge associated with a first-organism biochip device is characterized by: measuring a flow between an interior of the animal restraint cartridge and an exterior of the animal restraint cartridge. In another method embodiment, said exposing a second organism to the inhalent environment until a calculated second-organism delivered dosage meets or exceeds a predefined second-organism target dosage is characterized by: detecting the second organism via a second-organism biochip device implanted in the second organism; and recalling the predefined second-organism target dosage in response to the second-organism biochip device. In another method embodiment, said exposing a second organism to the inhalent environment until a calculated second-organism delivered dosage meets or exceeds a predefined second-organism target dosage is characterized by: measuring a volume respirated by the second organism; and calculating the delivered dosage in response to the volume. In another method embodiment, said measuring a volume respirated by the second organism is characterized by: measuring a volume of an animal restraint cartridge associated with a second-organism biochip device. In another method embodiment, said measuring a volume of an animal restraint cartridge associated with a second-organism biochip device is characterized by: measuring a flow between an interior of the animal restraint cartridge and an exterior of the animal restraint cartridge. In another method embodiment, said exposing a first organism to the inhalent environment until a calculated first-organism delivered dosage meets or exceeds a predefined first-organism target dosage is characterized by: coupling the inhalent environment to a first apertured connector containing at least a part of the first organism. In another method embodiment, said coupling the inhalent environment to a first apertured connector containing at least a part of the first organism is characterized by: starting a first-organism duration of time upon an initial coupling of the inhalent environment to the first apertured connector containing the at least a part of the first organism; and terminating the first-organism duration of time when the calculated first-organism delivered dosage meets or exceeds the predefined first-organism target dosage. In another method embodiment, said coupling the inhalent environment to a first apertured connector containing at least a part of the first organism is characterized by: opening a valve between the inhalent environment and the first apertured connector at a first-organism beginning time; and closing the valve between the inhalent environment and the first apertured connector at a first-organism ending time. In another method embodiment, said coupling the inhalent environment to a first apertured connector containing at least a part of the first organism is characterized by: closing a valve between a clean-air environment and the first apertured connector at a first-organism beginning time; and opening the valve between the clean-air environment and the first apertured connector at a first-organism ending time. In another method embodiment, said exposing a second organism to the inhalent environment until a calculated second-organism delivered dosage meets or exceeds a predefined second-organism target dosage is characterized by: coupling the inhalent environment to a second apertured connector containing at least a part of the second organism. In another method embodiment, said coupling the inhalent environment to a second apertured connector containing at least a part of the second organism is characterized by: starting a second-organism duration of time upon an initial coupling of the inhalent environment to the second apertured connector containing the at least a part of the second organism; and terminating the second-organism duration of time when the calculated second-organism delivered dosage meets or exceeds a predefined second-organism target dosage. In another method embodiment, said coupling the inhalent environment to a second apertured connector containing at least a part of the second organism is characterized by: opening a valve between the inhalent environment and the second apertured connector at a second-organism beginning time; and closing a valve between the inhalent environment and the second apertured connector at a second-organism ending time. In another method embodiment, said coupling the inhalent environment to a second apertured connector containing at least a part of the second organism is characterized by: closing a valve between a clean-air environment and the second apertured connector at a second-organism beginning time; and opening the valve between the clean-air environment and the second apertured connector at a second-organism ending time. In another method embodiment, the method is further characterized by performing an inhalent or exposure study, wherein said performing the inhalent or exposure study is characterized by said conditioning, said exposing a first organism, and said exposing a second organism. In addition to the foregoing, other method embodiments are described in the claims, drawings, and text forming a part of the present application.

In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer.

In one embodiment, a system includes but is not limited to: an inhalent manifold; a first independently-controllable exposure unit coupled to said inhalent manifold; a second independently-controllable exposure unit coupled to said inhalent manifold; and an exposure control system operably coupled to either or both said first independently-controllable exposure unit and said second independently-controllable exposure unit. In another system embodiment, said inhalent manifold is characterized by: an inhalent intake plenum operably coupled with an inner manifold. In another system embodiment, said inhalent manifold is characterized by: at least one environmental-condition sensor integral with said inhalent manifold, said at least one environmental condition sensor selected from an environmental-condition-sensor group including a temperature sensor, a relative humidity sensor, a pressure sensor, and an inhalent concentration sensor; and said exposure control system operably coupled to said at least one environmental-condition sensor. In another system embodiment, said inhalent manifold is characterized by: at least one environmental-condition controller integral with said inhalent manifold, said at least one environmental-condition controller selected from an environmental-condition-controller group including a temperature controller, a relative humidity controller, a pressure controller, and an inhalent concentration controller; and said exposure control system operably coupled to said at least one environmental-condition controller. In another system embodiment, said first independently-controllable exposure unit coupled to said inhalent manifold is characterized by: an independently-controllable valve interposed between the inhalent manifold and a first apertured connector; and said exposure control system operably coupled to said independently-controllable valve interposed between the inhalent manifold and a first apertured connector. In another system embodiment, said first independently-controllable exposure unit coupled to said inhalent manifold is characterized by: an independently-controllable valve interposed between the inhalent manifold and an exhaust manifold; and said exposure control system operably coupled to said independently-controllable valve interposed between the inhalent manifold and the exhaust manifold. In another system embodiment, said first independently-controllable exposure unit coupled to said inhalent manifold is characterized by: an animal restraint cartridge; a biochip device receiver integral with said animal restraint cartridge; and said exposure control system operably coupled to said a biochip device receiver. In another system embodiment, said first independently-controllable exposure unit coupled to said inhalent manifold is characterized by: an animal restraint cartridge; a differential volume sensor operably coupled to said animal restraint cartridge; and said exposure control system operably coupled to said differential volume sensor. In another system embodiment, said differential volume sensor operably coupled to said animal restraint cartridge is characterized by: a pneumotachograph operably coupled to said animal restraint cartridge; and a differential pressure transducer operably coupled to said pneumotachograph. In another system embodiment, said second independently-controllable exposure unit coupled to said inhalent manifold is characterized by: an independently-controllable valve interposed between the inhalent manifold and a second apertured connector; and said exposure control system operably coupled to said independently-controllable valve interposed between the inhalent manifold and the second apertured connector. In another system embodiment, said second independently-controllable exposure unit coupled to said inhalent manifold is characterized by: an independently-controllable valve interposed between the inhalent manifold and an exhaust manifold; and said exposure control system operably coupled to said independently-controllable valve interposed between the inhalent manifold and the exhaust manifold. In another system embodiment, wherein said second independently-controllable exposure unit coupled to said inhalent manifold is characterized by: an animal restraint cartridge; a biochip device receiver integral with said animal restraint cartridge; and said exposure control system operably coupled to said a biochip device receiver. In another system embodiment, said second independently-controllable exposure unit coupled to said inhalent manifold is characterized by: an animal restraint cartridge; a differential volume sensor operably coupled to said animal restraint cartridge; and said exposure control system operably coupled to said differential volume sensor. In another system embodiment, wherein said differential volume sensor operably coupled to said animal restraint cartridge is characterized by: a pneumotachograph operably coupled to said animal restraint cartridge; and a differential pressure transducer operably coupled to said pneumotachograph. In another system embodiment, wherein said exposure control system is characterized by: circuitry for (a) conditioning an inhalent environment in said inhalent manifold, (b) controlling said first independently-controllable exposure unit coupled to said inhalent manifold to expose at least a first organism to the inhalent environment for at least a first-organism duration of time, and (c) controlling said second independently-controllable exposure unit coupled to said inhalent manifold to expose at least a second organism to the inhalent environment for at least a second-organism duration of time; and said circuitry selected from an electrical-circuitry group including electrical circuitry having at least one discrete electrical circuit, electrical circuitry having at least one integrated circuit, electrical circuitry having at least one application specific integrated circuit, electrical circuitry having a general purpose computing device configured by a computer program, electrical circuitry having a memory device, and electrical circuitry having a communications device. In another system embodiment, said circuitry is characterized by: a data processing system running a control program.

In one embodiment, a method includes but is not limited to: detecting a first organism via a first-organism biochip device implanted in the first organism; and controlling a first-organism dosage in response to the first-organism biochip device. In another method embodiment, said detecting a first organism via a first-organism biochip device implanted in the first organism is characterized by: detecting transmission from the first-organism biochip device via a receiver paired with a predefined animal restraint cartridge. In another method embodiment, said controlling a first-organism dosage in response to the first-organism biochip device is characterized by: recalling the predefined first-organism target dosage in response to the first-organism biochip device; and exposing the first organism to an inhalent environment until a calculated first-organism delivered dosage meets or exceeds a predefined first-organism target dosage. In another method embodiment, said exposing a first organism to the inhalent environment until a calculated first-organism delivered dosage meets or exceeds a predefined first-organism target dosage is characterized by: measuring a volume respirated by the first organism; and calculating the first-organism delivered dosage in response to the volume. In another method embodiment, the method is further characterized by: detecting a second organism via a second-organism biochip device implanted in the second organism; and controlling a second-organism dosage in response to the second-organism biochip device. In another method embodiment, said detecting a second organism via a second-organism biochip device implanted in the second organism is characterized by: detecting transmission from the second-organism biochip device via a receiver paired with a predefined animal restraint cartridge. In another method embodiment, said controlling a second-organism dosage in response to the second-organism biochip device is characterized by: recalling the predefined second-organism target dosage in response to the second-organism biochip device; and exposing the second organism to an inhalent environment until a calculated second-organism delivered dosage meets or exceeds a predefined second-organism target dosage. In another method embodiment, said exposing a second organism to the inhalent environment until a calculated second-organism delivered dosage meets or exceeds a predefined second-organism target dosage is characterized by: measuring a volume respirated by the second organism; and calculating the second-organism delivered dosage in response to the volume. In addition to the foregoing, other method embodiments are described in the claims, drawings, and text forming a part of the present application.

In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE SEVERAL VIEWS OF THE DRAWING(S)

Figure 4:
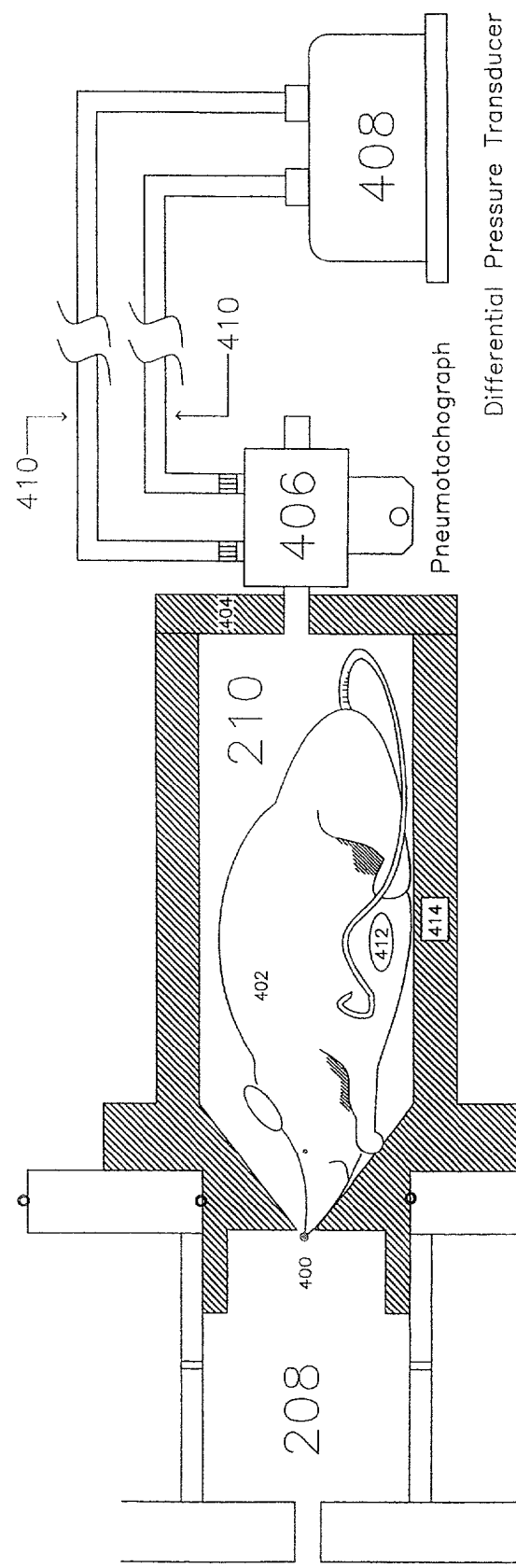

FIG. 4 shows a drawing of animal restraint cartridge 210 and associated hardware. FIG. 4 also shows a biochip identification device 412, implanted in animal 402 and preprogrammed with an electronic identifier unique to animal 402.

The use of the same symbols in different drawings typically indicates similar or identical items

DETAILED DESCRIPTION OF THE INVENTION

A. Devices

Figure 1:
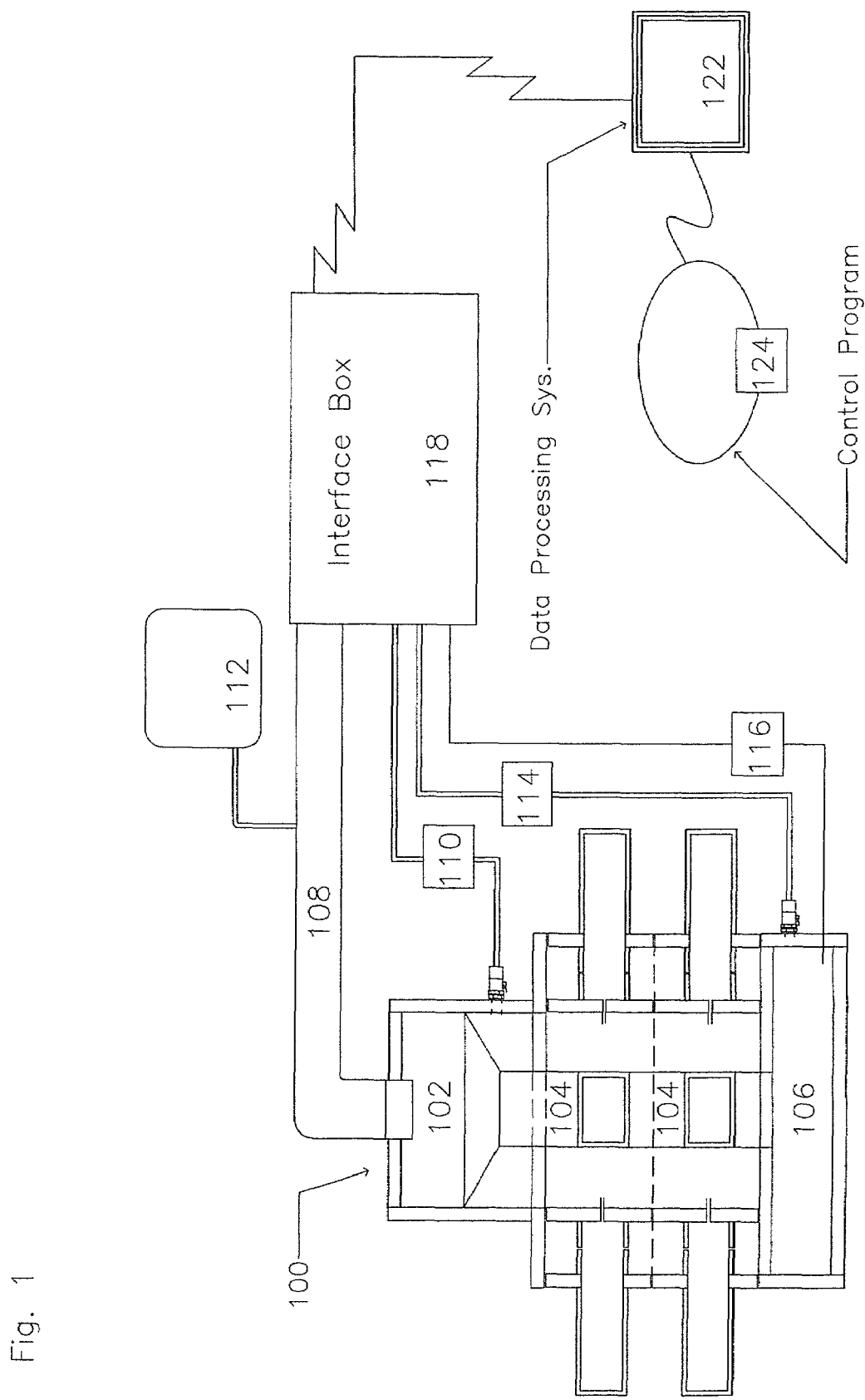
FIG. 1 shows a high level pictographic representation of an exposure system and associated hardware.

A high level pictographic representation of an exposure system and associated hardware is included as FIG. 1. Depicted is exposure tower 100 composed of three distinct sections: input module 102, exposure modules 104, and exhaust module 106. Shown connected to the input module are inhalent air input hose 108 and clean air input hose 110. Integral with inhalent air input hose 108 is inhalent dissemination device 112. Inhalent dissemination device 112 is meant to be indicative of a variety of different devices for dispersing organic or inorganic substances in an aerosol, gas, fume, dry powder, or other suitable form. Connected to exhaust module 106 is output air hose 114. Shown coupled to exposure tower 100 is also wire bundle 116, meant to be indicative of a plurality of wires connecting a variety of electronic devices housed in exposure tower 100 to interface box 118. Operably coupled to interface box 118 are also inhalent input air hose 108, clean air input hose 110, and output air hose 114. Interface box 118 houses the necessary power supplies, input airflow drivers, output airflow drivers, data acquisition hardware, and other associated electronics for the electronic devices in exposure tower 100. Further illustrated is interface box 118 operably coupled to data processing system 122. Residing in and running on data processing system 122 is specially developed control program 124 where such control program controls the various drivers, sensors, and other electronic devices in interface box 118 and exposure tower 100.

Figure 2:
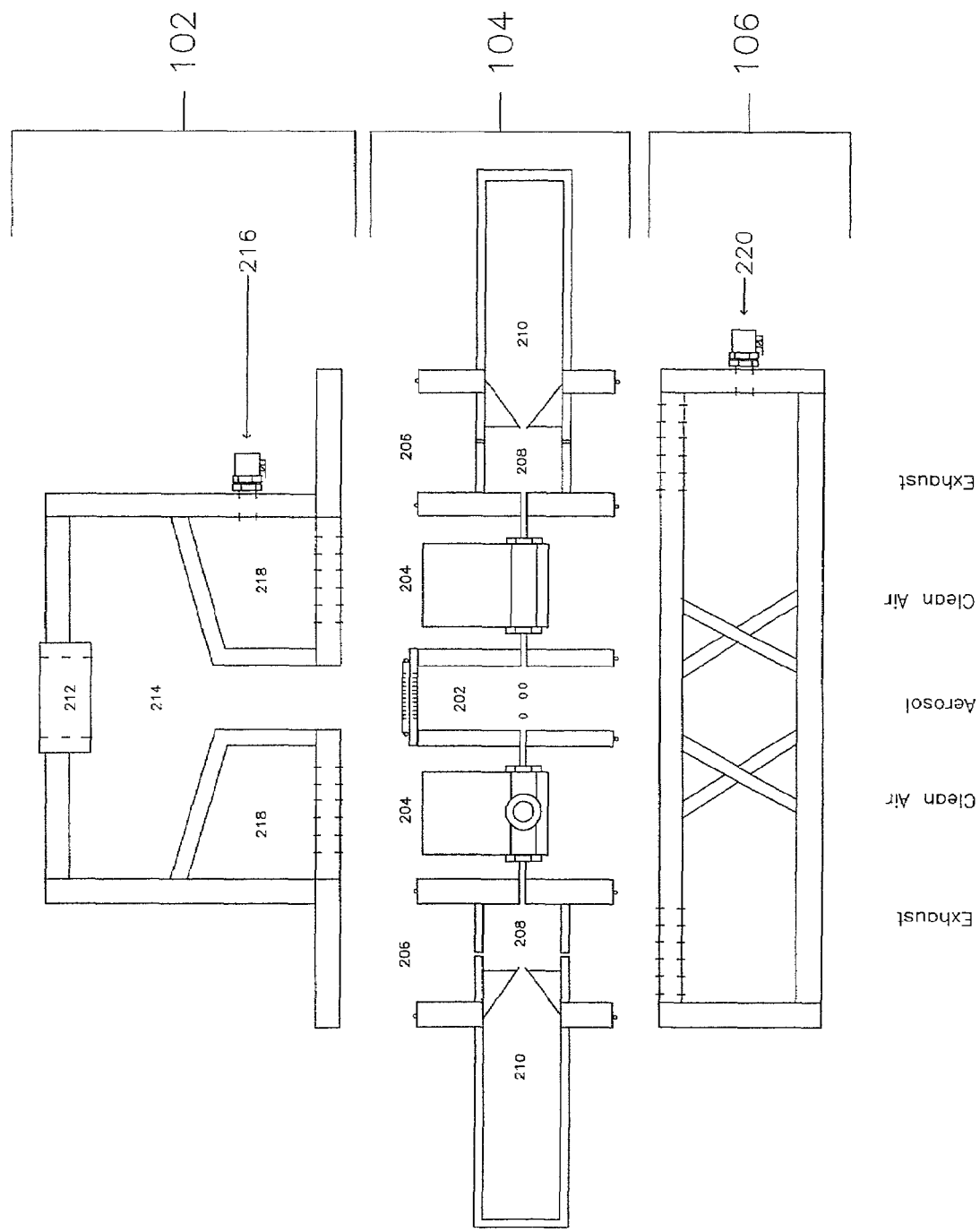
FIG. 2 depicts a pictographic representation of exposure tower 100.

With reference now to FIG. 2, depicted is a pictographic representation of exposure tower 100. Shown are cutaway drawings of input module 102, exposure module 104, and exhaust module 106. Exposure module 104 is composed of three concentric manifolds all composed of nonporous, autoclavable, non-reactive materials: inner manifold 202, middle manifold 204, and outer manifold 206. A plurality of annular shaped apertured connectors 208 are housed in outer manifold 206. Each apertured connector is designed to support and mate with animal restraint cartridge 210 inserted from outside the outer manifold. A plurality of identical exposure modules 104 can be stacked between input module 102 and exhaust module 106 as necessary to accommodate the number of animals to be included in any particular study.

Input module 102 includes coupler fitting 212 which mates with inhalent air input hose 108 (not shown in FIG. 2) and provides the mechanism for introducing the inhalent into inhalent intake plenum 214 and, hence, into inner manifold 202 of exposure module 104. Also provided with input module 102 is coupler fitting 216, designed to be operably coupled with clean input air hose 110 (not shown in FIG. 2) and providing the mechanism for introducing clean, filtered air into clean air intake plenum 218 and, hence, into middle manifold 204 of exposure module 104.

Further with respect to FIG. 2 is depicted a cutaway drawing of exhaust module 106. Exhaust module 106 is provided with coupler fitting 220 which mates with output air hose 114 (not shown in FIG. 2) and provides the mechanism for exhausting air from exhaust module 106 and, hence, outer manifold 206 of exposure module 104.

Figure 3:
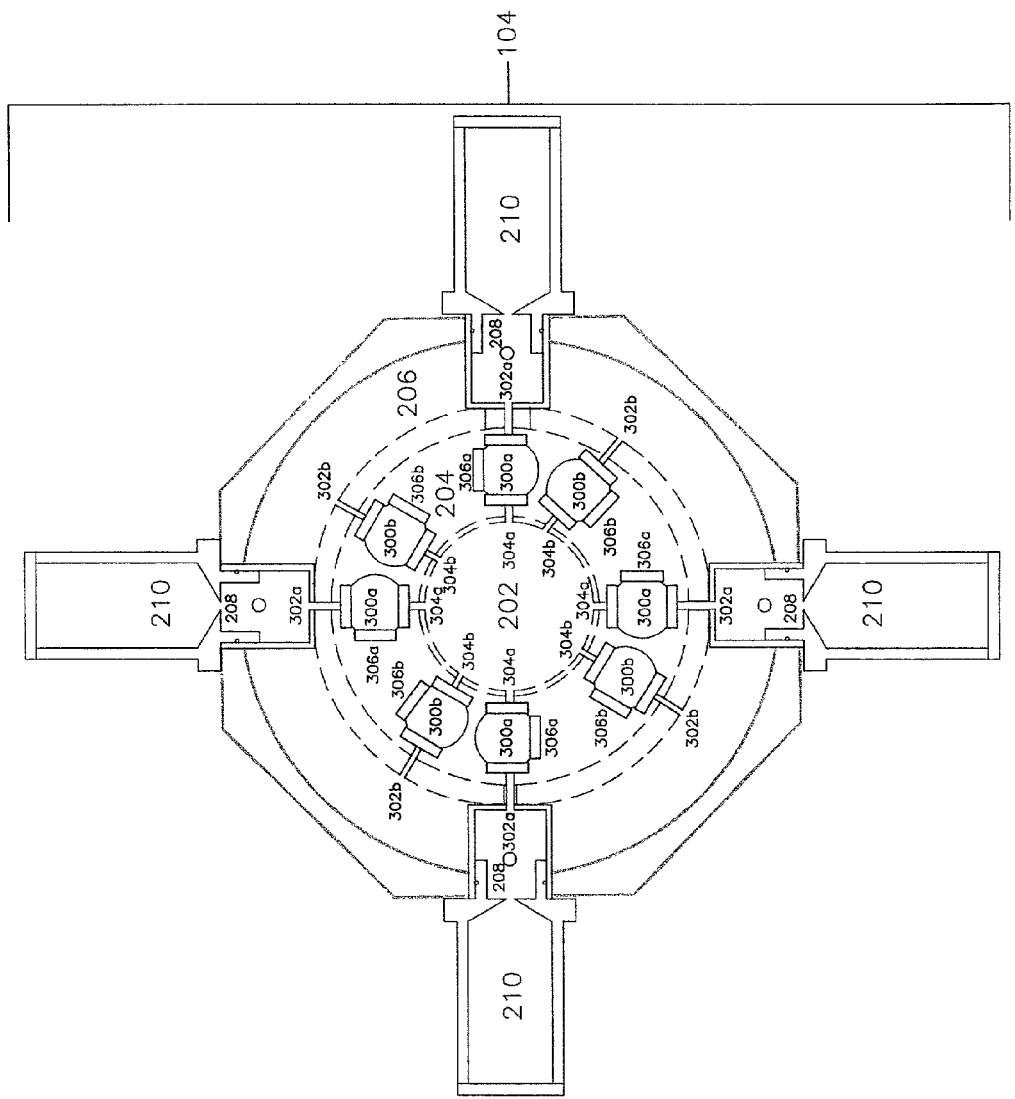
FIG. 3 illustrates a top view drawing of exposure module 104.

Depicted in FIG. 3 is a top view drawing of exposure module 104. Shown in FIG. 3 is that housed in middle manifold 204 are electronically controlled three-way valves 300a and 300b, each associated with an apertured connector 208. Valve 300a is oriented such that outlet 302a is plumbed to apertured connector 208, inlet 304a is plumbed to inner manifold 202, and inlet 306a is open to middle manifold 204. Valve 300b is oriented such that outlet 302b is plumbed to outer manifold 206, but not into apertured connector 208, inlet 304b is plumbed to inner manifold 202, and inlet 306b is open to middle manifold 204. Valves 300a and 300b are coupled to interface box 118 via wire bundle 116 and controlled by means of control program 124 running on data processing system 122 (not shown in FIG. 3).

This assembly of valves 300a and 300b allows each pair to be electronically switched via control program 124 into either a "bypass" condition or an "expose" condition. In the bypass condition, valve 300a is set so that clean air from middle manifold 204 flows into inlet 306a, out of outlet 302a, through apertured connector 208, and into outer manifold 206. In the bypass condition valve 300b is set so that the inhalent atmosphere in inner manifold 202 flows into inlet 304b, out of outlet 302b, and directly into outer manifold 206. In the expose condition valve 300a is set such that the inhalent atmosphere in inner manifold 202 flows into inlet 304a, out of outlet 302a, through apertured connector 208, and into outer manifold 206. In the expose condition valve 300b is set so that clean air from middle manifold 204 flows into inlet 306b, out of outlet 302b, and directly into outer manifold 206. Those having ordinary skill in the art will appreciate that the herein described dual-valve design allows the throughput of the inhalent to remain substantially constant, in that when an animal's exposure to an inhalent from the inhalent manifold (e.g., the inhalent intake plenum 214 operably coupled with the inner manifold 202) is terminated, the part of the inhalent throughput that was being routed past the animal is instead routed to the exhaust, and in that when an animal's exposure to an inhalent from the inhalent manifold (e.g., the inhalent intake plenum 214 operably coupled with the inner manifold 202) is began, the part of the inhalent throughput that was being routed to the exhaust is instead routed past the animal.

With reference now to FIG. 4, depicted is a drawing of animal restraint cartridge 210 and associated hardware. Shown is opening 400 through which the nose of animal 402 extends into the chamber formed in apertured connector 208. Further demonstrated is end cap 404 which is sealed after animal 402 is positioned in restraint cartridge 210 with its nose extending through opening 400. Integral with end cap 404 is pneumotachograph 406 extending into restraint cartridge 210. Pneumotachograph 406 is operably coupled to pressure transducer 408 by tubes 410. Pressure transducer 408 is coupled to interface box 118 via wire bundle 116 and monitored by control program 124 running on data processing system 122 (not shown in FIG. 4). When animal 402 is positioned in restraint cartridge 210 with its nose through opening 400 and end cap 404 is sealed, an airtight chamber is formed. The pneumotachograph/pressure transducer combination measures the flow of air to and from restraint cartridge 210 in real-time as animal 402's thoracic cage expands and contracts with respiratory function. These flow measurements are processed by control program 124 to calculate respiratory tidal volume, respiratory rate, respiratory minute volume, and cumulative tidal volume in near-real time for each animal simultaneously and independently.

An example calculation, using the foregoing-described mechanisms, would be as follows. A rodent inside restraint cartridge 210 inhales 120 μl of air, thus expanding its thoracic cage. This thoracic cage expansion results in 120 μL of air passing from restraint cartridge 210, through pneumotachograph 406 to the outside environment in the approximately 0.1 sec inhalation time for the rodent. For a pneumotachograph with an approximately 2 mm$^2$ cross-section, this 1.2 mL/sec flow generates a pressure differential of approximately 0.03 WC" (water column inches). In response to this differential, pressure transducer 408 generates an electrical current of 1.1 mA measured by the computer hardware in interface box 118 and processed by control program 124 running on data processing system 122.

Upon receiving the 1.1 mA signal, control program 124 calls a calibration look up table, stored on data processing system 122 and scales the current to the 120 μL tidal volume (TV) that the rodent originally inhaled. In one implementation, the calibration table is created and stored during initial system development and is generated via use of an appropriate rodent ventilator.

In one implementation, in order to generate the calibration table a ventilator is connected to the nose port of restraint cartridge 210, and a rodent-sized phantom is placed inside. The ventilator is then run at various respiratory rates and tidal volumes characteristic of the rodent pulmonary function. For each respiratory rate and tidal volume setting, the current generated by differential pressure transducer 408 is measured. The scaling factor needed to convert the current reading to the original tidal volume is then assigned to that particular set of respiratory parameters. Applying this process to the full range of relevant tidal volumes and respiratory rates generates a matrix of calibration scaling values. These values are stored in a spreadsheet file. Based on the current generated and the respiratory rate for each successive breath, control program 124 references the spreadsheet file to scale the current reading from pressure transducer 408 appropriately. Alternatively, a mathematical fit can be applied to the calibration data matrix described, thus generating a formula that applies a scaling factor appropriate to a particular tidal volume and respiratory rate measured.

Successive tidal volume measurements are added by control program 124 to generate a running cumulative tidal volume (CTV) total. The time between successive breaths is also measured via a timer feature inherent to control program 124, and used by control program 124 to calculate respiratory rate (RR) and minute volume (MV). Respiratory rate is calculated by dividing 60 by the time between successive breaths in seconds. Minute volume is calculated by multiplying tidal volume by the respiratory rate. The following is an example of how successive tidal volume measurements, made using the methodology described, are used to calculate these parameters:

| Time (sec) | TV (mL) | CTV (ml) | RR (b/min) | MV (mL/min) |
|---|---|---|---|---|
| 0.00 | 0.120 | 0.120 | — | — |
| 0.25 | 0.180 | 0.300 | 240 | 43.2 |
| 0.48 | 0.160 | 0.460 | 260 | 41.6 |
| 0.68 | 0.172 | 0.612 | 300 | 51.6 |
| 0.90 | 0.148 | 0.760 | 272 | 40.2 |
| 1.15 | 0.140 | 0.900 | 240 | 33.6 |

Note that RR and TV cannot be calculated for the first breath. Since these parameters depend on the rate of breathing, at least two measurements are required for their calculation.

Further with respect to FIG. 4 is biochip identification device 412, shown implanted in animal 402 and preprogrammed with an electronic identifier unique to animal 402. Also shown integrated into restraint cartridge 210 is electronic receiver device 414. Receiver device 414 reads the electronic signal from biochip device 412 and identifies animal 402. Receiver device 414 is coupled to interface box 118 via wire bundle 116 (not shown in FIG. 4), providing the means for control program 124 running on data processing system 122 to identify animal 402 in restraint cartridge 210.

B. Description of System Operation:

When utilizing the system the operator first loads animals implanted with biochip identification device 412 into restraint cartridges 210. When restraint cartridges 210 are inserted into apertured connectors 208, receiver devices 414 read the signals emitted from biochip devices 412 and automatically identifies the animal in each individual restraint. These identifications are transmitted through wire bundle 116 into interface box 118 and to data processing system 122. Control program 124 recalls a dose schedule from a data base stored in data processing system 122 or entered by the user and, based on the identity of the animal in each restraint, identifies the inhalent dose that each animal is to receive.

After all animals are loaded into apertured connectors 208 and identified, the user initiates the exposure sequence via the graphical user interface of data processing system 122. Control program 124 switches all valve pairs 300a and 300b to the bypass condition, activates aerosol dissemination device 114, and initiates the flows through inhalent air input tube 108, clean air input tube 106, and output air tube 110.

Additionally, control program 124 initiates monitoring of the environmental conditions (temperature, relative humidity, pressure, inhalent concentration, etc.) in inner manifold 202 via a plurality of sensors housed in interface box 118 and in inner manifold 202. Control program 124 also electronically manages a variety of devices (a humidification device, a heating/cooling device, an inhalent dissemination device, flow controlling devices, etc.) as necessary to achieve and maintain said environmental conditions at levels defined by the user. Since all valve pairs 300a and 300b are in the bypass condition, all animals are supplied with clean filtered air from middle manifold 204 and not exposed to the inhalent while control program 124 achieves the user defined environmental conditions in inner manifold 202.

Once all of the environmental conditions entered by the user are achieved in inner manifold 202, control program 124 initiates the animal exposure by electronically switching all valve pairs 300a and 300b to the expose condition. Additionally, control program 124 initiates the comprehensive respiratory monitoring algorithm for each animal utilizing the electronic signals generated by pressure transducers 408. The algorithm simultaneously monitors the cumulative tidal volume for every animal being exposed in near real-time. Control program 124 uses this cumulative tidal volume measurement in conjunction with the inhalent concentration measurement acquired by environmental monitoring devices to calculate the actual inhaled dose of the inhalent for each animal in near real-time.

When an individual animal's inhaled dose as measured by the respiratory monitoring algorithm of control program 124 equals that called for by the dose schedule recalled via the animal identification system, control program 124 switches valve pair 300a and 300b corresponding to that animal from the expose to the bypass condition. Meanwhile, valve pairs 300a and 300b corresponding to other animals remain in the expose condition. Other animals continue to be exposed until the respiratory monitoring algorithm of control program 124 indicates that they have inhaled the dose required by the dose schedule/identification algorithm. Control program 124 switches each valve pair 300a and 300b to the bypass condition when its corresponding animal has received the scheduled dose. When the required doses are achieved for all animals and all valve pairs 300a and 300b are in the bypass condition, control program 124 deactivates aerosol dissemination device 114, and terminates the flows through inhalent air input tube 108, clean air input tube 106, and output air tube 110. Control program 124 notifies the user via an audible signal and a visible indication on the graphical user interface of data processing system 122 that the exposures for all animals are complete.

In addition to controlling all aspects of the exposure described above, control program 124 writes, at a frequency defined by the user, all environmental, flow, respiratory, and identification data to a file for subsequent analysis. Additionally, all operator keystrokes and actions initiated and terminated by control program 124 are logged in a second file for record keeping and quality control purposes.

Those having ordinary skill in the art will appreciate that while there are many fields of application wherein the processes and devices described herein will prove advantageous. One particularly advantageous field of application is that of inhalant and/or exposure studies. Various examples of how the processes and devices described herein may be used in inhalant and/or exposure studies are described in the following Addendum A.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which aspects of processes and/or systems described herein can be effected (e.g., hardware, software, and/or firmware), and that the preferred vehicle will vary with the context in which the processes and/or systems are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which aspects of the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and examples. Insofar as such block diagrams, flowcharts, and examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. In one embodiment, the present invention may be implemented via Application Specific Integrated Circuits (ASICs). However, those skilled in the art will recognize that the embodiments disclosed herein, in whole or in part, can be equivalently implemented in standard Integrated Circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into data processing systems. That is, the devices and/or processes described herein can be integrated into a data processing system via a reasonable amount of experimentation.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

From the foregoing it will be appreciated that, although specific embodiments of the invention have been described herein for purposes of illustration, various modifications may be made without deviating from the spirit and scope of the invention. Accordingly, the invention is not limited except as by the appended claims.

Addendum A

Applications of Processes and Devices Described Herein

Those skilled in the art will recognize that the following example applications are intended to be exemplary and non-limiting. Those skilled in the art will recognize that many other applications are possible based on the teachings herein.

I. Those skilled in the art will appreciate that, in the context of preclinical animal studies involving various materials under testing (MUT), which may include, but are not limited to, new chemical entities (NCEs), biologically-derived products (biologics), and miscellaneous MUTs such as environmental contaminants, various implementations of the processes and devices described herein can be utilized to significantly reduce the inputs to such preclinical animal studies. Those skilled in the art will appreciate that such inputs may include but are not limited to time, cost, dose uncertainty, and physical space requirements to accomplish said procedure(s) associated with absorption, distribution, metabolism, and excretion (ADME), toxicology, pharmacology and other miscellaneous studies that require MUTs to be administered by inhalation.

a. Preclinical Safety and Efficacy Studies for MUTs Including NCEs and Biologics. In general, a series of animal studies must be performed to satisfy regulatory requirements of various codified regulations promulgated by national and international organizations (e.g., USFDA, EUCOM) whereas a MUT must be administered to selected animal species in specified lengths of time, which may include acute (one time administration), subchronic (repeated administration up to 90 days), and chronic administration (up to two years), usually in at least two different species of animal, which may include rodents (e.g., mice, rats, guinea pigs), dogs, rabbits, and nonhuman primates to ensure safety and efficacy of the MUT as one of the requisite experimental steps for the MUT to be administered in the human population to inhibit the effects of or cure disease. Preclinical studies (experimental studies with animals) are performed prior to clinical studies, that is experimental studies with selected human populations, to assess safety and efficacy of a MUT. Generally, these procedures are performed in rodents at least preliminarily, mainly because of cost and acquisition considerations. In the case of MUTs whose indication, that is the administration route, is inhalation, an exposure 'system' must be employed to accomplish dosing (e.g., administering the MUT internally into the selected animal that is provided in a volumetric concentration into the organism and expressed as a proportional to the body weight of the said organism) of animals, which is usually performed at multiple dosages to establish a variety of predicted biological outcome such as organ toxicity, enzymatic changes, lethality, therapeutic index, pharmacodynamics/kinetics, and dose-response curves. Each dosage group of a particular species or animal usually consists of a statistically-derived number of animal based on the predicted biological outcome, a typical number being 10 animals per dosage group. If multiple doses are performed, for example three plus a control group, with a control group being defined as a group of animals experiencing the administration method of cohort dosage groups but not actually receiving the MUT per se and rather receiving the inert vehicle in which the MUT is combined with for the purposes of dosing procedures (i.e., clean air), receiving and the study is performed in two species of animals, for example, rats and mice, then a typical number of animals included on a study for one biological outcome is 80.

i. Performance of inhalation preclinical studies utilizing 'traditional' dosing systems. Continuing on the assumed number of rodents needed to accomplish a study, for example a 90-day repeated dosing study containing three dosage groups plus a control group, each per species, each group consisting of 10 animals, to determine the resulting toxicological effects, if any, of an MUT that culminates in sacrifice of all animals +91 'days' after completion of the study. In general, most exposure systems used to accomplish repeated dosing consist of a dynamic chamber, that is an exposure chamber that introduces a flow of air into the chamber housing the animal (or parts thereof) and exhausts the contaminated air at a rate congruent to the introduction, usually, allowing for a residence time that will allow inhalation of the aerosolized MUT by the animals at a particular rate congruent to a predetermined dose. In general, one skilled in the art will generally acknowledge that each 'daily' dosing regime of a particular dosage group of animals exposed to a particular concentration of MUT to achieve a particular dose will usually consume at least 0.5 of a standard workday (four hours) from set-up to returning the animals to their cages until the next dosing. In general, each dosing experiment for the eight dosage groups (three dosages plus control per species using two species) would be accomplished separately (or at least in separate exposure systems requiring equivalent personnel and MUT). In addition, if one were to use either a singular or a battery of aerosol generation devices to provide the necessary MUT entrained into the experimental atmosphere for a singular or battery of inhalation exposure systems, separate measurements of said atmospheres, which may include characterization of the aerosol delivered to the animals in the dosing group(s) which includes relative (single or multiple) concentration determination of the MUT in the experimental atmosphere provided to the animal to be internalized via respiration which would equate to development of an 'inhaled' dose delivered daily during the 90 day repeated dosing study of the hypothetical study, would be necessitated because of the nature of the dosing procedures associated with experimentally similar, but uniquely separate generation of aerosols into a single or battery of inhalation exposure systems. In addition, the use of a single or battery of exposure systems would require different laboratory physical space requirements. One skilled in the art would tend to acknowledge that of the commercially-available or custom-built rodent inhalation systems, a physical footprint of a single system (assuming an infinite vertical plane), including all ancillary equipment associated with the hypothesized single inhalation system, would tend to measure a minimum of 25 cubic feet (cu. ft).

1. Estimation of time, cost, dosing uncertainty, and space requirements using traditional inhalation systems. The time required to accomplish a single daily dose to all groups (two species, each consisting of three dosage groups plus a species-specific control group) would equate to four (4.0) standard workdays per dosage 'day' as prescribed from the assumed 90 day study design, which exceeds the intended '90' days for the '90' day repeated dosage study. Utilizing the assumptions in the example, a total of 360 standard workdays would be required to accomplish the 90 day repeated dosing regime portion prescribed by study design, acknowledging that one using a battery of exposure systems, say eight, to accomplish the daily dose could simultaneously accomplish all the prescribed dosage groups at the same time in the same actual workday, the personnel and associated support to perform this task will be equivalent to the assumed 0.5 standard workday, although time on the temporal scale for the aforementioned experimental scenario would not be congruent to one using a single exposure inhalation system attempting to accomplish the study. Building on the presented example, if one skilled in the art were to endeavor upon performing such a study, and had and singular or battery of inhalation exposure system(s) at disposal to accomplish the experiment, this would necessitate eight separate inhalation administrations per dosing 'day' for a prescribed 90 day repeated dosing study for a total minimum of 720 dosing experimental procedures, assuming no errors of personnel or experimental flaws in the dosing administration, as defined by a single dose administered to an animal dosage group on one of the 90 days in the repeated dosing experimental design. If one were to assign an arbitrary all-inclusive cost per hour that comprises a hypothetical eight-hour workday of $1000 ($8,000 per day), the cost of accomplishing a 90 day dosing study using an exposure system or a battery thereof would be estimated at $2,800,000 ($2.8M). If one were to assign the measurements associated with determining the aerosol concentration in the experimental atmosphere(s) generated during the 720 dosing administrations associated with the prescribed study design, which one skilled in the art would acknowledge is usually performed at least three times per exposure, generally to determine an average and inherent width of the confidence interval associated with said measurements, usually, expressed in some format of a standard deviation of said measurements, usually defined as the positive square root of the total variance of all of the uncertainty[1] components combined, over the time associated with administering the prescribed dosage, would total 2,160 individual measurements. Introduction of uncertainty of the measurements is inherent due to the sheer number of the measurements taken during the daily dosings, generally defined by the tenets of method validation, comprising parameters among others such as bias, linearity, detection limits, and robustness of measurements, most importantly in this context being precision, being generally defined as the reproducibility of a result either within a laboratory or operator, equipment (i.e., inhalation exposure system(s)) and accuracy, being generally defined as the closeness of the result that was originally intended at the initiation of a particular inhalation procedure, in this case the dosing of each animal group. Finally the space requirements associated with accomplishing the said dosing of the prescribed study would be, assuming a single or battery of, for example eight, exposure system(s) would require 25 or 200 sq. ft. of laboratory space, respectively.

[1] Uncertainty of measurement dose not imply doubt about the validity of a measurement; on the contrary, knowledge of the uncertainty implies increased confidence in the validity of the measurement result. From: EURACHEM/CITAC Guide. *Quantifying Uncertainty in Analytical Measurement*, Second Edition, Ed. Ellison, SLR, 2000.

ii. Performance of preclinical study with the described processes and device. As described by the processes and devices herein, the processes and devices allow simultaneous daily dosing of all groups and species (assuming that the other species is on the equivalent phylogenetic scale) based on the electronic monitoring of the individual animals' respiration all within the same exposure system and aerosol stream. The processes and devices, as described herein, assuming an infinite vertical plane, would significantly reduce the four aforementioned conditions of time, cost, dosing uncertainty, and space requirements over using traditional inhalation systems.

1. Usage of the said processes and devices, as described herein, to accomplish the equivalent dosing regime prescribed in the hypothetical example would allow dosing of all eight dosage groups (80 animals total) all within the typical 0.5 standard workday, which is an obvious improvement of one attempting to accomplish daily dosing with a single traditional inhalation system, but the time savings over one using the alternative scenario (a battery of inhalation systems) cannot be measured on the temporal scale to realize inherent time savings based on characteristics inherent to performing simultaneous dosing procedures using multiple inhalation exposure systems, all intrinsically requiring some form of simultaneous attention from user resources (i.e., laboratory personnel) to successfully perform daily dosing, which assuming that each system requires equivalent resources for the various functioning components including, but not limited to loading of the animals into separate systems, aerosol generation, aerosol characterization, monitoring of animals, one skilled in the art would acknowledge that this equates to individual, say eight, separate exposures being performed, albeit at the same time, resulting in an estimate of 360 standard workdays using traditional inhalation system(s). The processes and devices, as described herein, in one implementation relies on one physical unit, which each animal's individual dose is controlled, and all of the experimental atmosphere containing the MUT is being provided to the animals at the same time from the same aerosol generation source. Assuming the hypothetical experimental design, the '90' day repeated dosing study would theoretically be reduced to 45 standard workdays which is based on all exposure groups loaded into the same exposure system at the same time and the dosing, assuming the highest dosage group will be achieved within the assumed 0.5 standard workday. Building upon the demonstrated time savings using the processes and devices as described herein, and assuming the assigned arbitrary $1000 per hour/workday rate to accomplish this study, the total cost for the study would be $360,000 based upon 45 standard workdays, comprised of a hypothetical eight hour workday for performance of dosing of all groups for a '90' day repeated study. The uncertainty, defined by precision and accuracy, associated with the daily dosing in the context of the 90 day repeated dosing regime, would be inherently minimized based on both the exquisite control exhibited over each individual animal's dosing and the reduction of the necessity of separate aerosol generation using traditional inhalation system(s). The total number of aerosol generation procedures associated with daily dosing, that would consequently be characterized, would be 90. The space associated with the processes and devices described herein, one implementation, would occupy 25 sq. ft. and be equivalent to a single traditional inhalation system. No further ancillary space is needed, as the processes and devices as described herein, assuming an infinite vertical plane, would emulate a traditional single inhalation system in outward appearance.

iii. Summary of direct comparison between traditional inhalation systems and one implementation of the processes and devices, as described herein, with respect to time, cost, uncertainty of dose, and space requirements. The time savings that would be realized via the usage of one implementation of the processes and devices, as described herein, would be advantageous over traditional systems currently being utilized for animal studies similar to the example. Performance of the study with of one implementation of the processes and devices would require 45 standard workdays, or 360 hours, to accomplish the study; a total of 360 workdays, or 2,880 hours, would be required using either a single or a battery of traditional inhalation systems. Using of one implementation of the processes and devices over traditional inhalation system(s) would result in a time savings to the user of 315 standard workdays, or 2,520 hours to accomplish the 90 day study, assuming equivalency (two species of animals, each consisting of three dosage groups plus a species control (8 groups total)). Building upon the time savings demonstrated, assuming the hypothetical $1000 per hour ($8,000 per standard workday), performing the study using of one implementation of the processes and devices would cost $360,000; using traditional inhalation systems would theoretically cost $2.8M. Using of one implementation of the processes and devices results in a cost savings to the user of $2.44M. In other terms, performing the 90 day study using of one implementation of the processes and devices only costs approximately 12% of the theoretical cost of performing the study with a traditional exposure system or battery of systems. Uncertainty of dosing would be vastly minimized utilizing of one implementation of the processes and devices over traditional systems, primarily due to monitoring each individual animal's dose, which is an aspect of traditional systems that is not available within the state of the art (at least in a simultaneous dosing scenario). Uncertainty of dosing would be inherently reduced due to the reduction of number of samples that are taken from the generated aerosol for daily dosing of the animals. Measurements of the experimental atmospheric concentration during the 90 separate aerosol generation procedures, using one implementation of the processes and devices, assuming a minimum of three measurements per generation to determine an average and variance of experimental atmospheric concentration, would total 180; traditional inhalation systems would require 720 independent aerosol generation procedures, either single or a battery, assuming equivalency with respect to minimum sampling number per aerosol generation procedure, would require 2,160 measurements. The number of samples needed to characterize the concentration of the aerosol generated for purposes of dosing the animals using one implementation of the processes and devices, as described herein, is reduced by 1,980 samples, or approximately 9% of the number of samples needed to characterize traditional systems. Although the advantages of one implementation of the processes and devices, as described herein, with respect to precision and accuracy demand empirical determination, one skilled in the art would acknowledge that a minimization of the separate aerosol generation procedures and subsequent number of samples needed to characterize the experimental atmosphere designed to deliver a dose will inherently increase precision and accuracy of the dosing of animal groups in the study. The physical space requirements in the laboratory to utilize one implementation of the processes and devices, as described herein, is estimated at 25 sq. ft., this is equivalent to a single traditional inhalation system, although to attain the capacity of dosing of animal groups that is congruent and subsequently comparable with one implementation of the processes and devices, as described herein, would require eight traditional inhalation systems, which would require 200 sq. ft. of physical space. The space requirements using one implementation of the processes and devices, as described herein, is reduced by 175 sq. ft., or approximately 12% of the space requirements of the battery of traditional inhalation systems needed to attain the simultaneous capacity of one implementation of the processes and devices, as described herein.

The invention claimed is:

1. A method comprising:
   conditioning an inhalent environment;
   exposing a first organism to the inhalent environment for a first-organism duration of time, exposing including
   disconnecting a clean-air supply from a first apertured connector, containing at least a part of the first organism, and
   coupling the inhalant environment to the first apertured connector for the first-organism duration of time; and
   exposing a second organism to the inhalent environment for a second-organism duration of time.

2. The method of claim 1, wherein said coupling the inhalent environment to a first apertured connector, containing at least a part of the first organism, for the first-organism duration of time comprises:
   starting the first-organism duration of time upon an initial coupling of the inhalent environment to the first apertured connector containing the at least a part of the first organism; and
   terminating the first-organism duration of time when a calculated first-organism delivered dosage meets or exceeds a predefined first-organism target dosage.

3. The method of claim 2, wherein said terminating the first-organism duration of time when a calculated first-organism delivered dosage meets or exceeds a predefined first-organism target dosage comprises:
   detecting the first organism via a first-organism biochip device implanted in the first organism; and
   recalling the predefined first-organism target dosage in response to the first-organism biochip device.

4. The method of claim 2, wherein said terminating the first-organism duration of time when a calculated first-organism delivered dosage meets or exceeds a predefined first-organism target dosage comprises:
   measuring a volume respirated by the first organism;
   calculating the first-organism delivered dosage in response to the volume.

5. The method of claim 4, wherein said measuring a volume respirated by the first organism comprises:
   measuring a volume of an animal restraint cartridge associated with a first-organism biochip device.

6. The method of claim 5, wherein said measuring a volume of an animal restraint cartridge associated with a first-organism biochip device comprises:
   measuring a flow between an interior of the animal restraint cartridge and an exterior of the animal restraint cartridge.

7. The method of claim 1, wherein said coupling the inhalent environment to a first apertured connector, containing at least a part of the first organism, for the first-organism duration of time comprises:
   opening a valve between the inhalent environment and the first apertured connector at a first-organism beginning time; and
   closing the valve between the inhalent environment and the first apertured connector at a first-organism ending time.

8. The method of claim 2, wherein said coupling the inhalent environment to a first apertured connector, containing at least a part of the first organism, for the first-organism duration of time comprises:
  closing a valve between a clean-air environment and the first apertured connector at a first-organism beginning time; and
  opening a valve between the clean-air environment and the first apertured connector at a first-organism ending time.

9. A method comprising:

automatically conditioning an inhalent environment to achieve a predetermined environmental condition;

distributing to a first organism the conditioned inhalent environment for a first-organism duration of time;

distributing to a second organism the conditioned inhalent environment for a second-organism duration of time, distributing to a second organism includes coupling the inhalent environment to a second apertured connector containing at least a part of the second organism for the second-organism duration of time, coupling the inhalent environment to a second apertured connector includes starting the second-organism duration of time upon an initial coupling of the inhalent environment to the second apertured connector containing the at least a part of the second organism, and terminating the second-organism duration of time when a calculated second-organism delivered dosage meets or exceeds a predefined second-organism target dosage; and wherein the first organism and the second organism are exposed to the same conditioned inhalant environment after the inhalent environment has been completely conditioned.

10. The method of claim 9, wherein said terminating the second-organism duration of time when a calculated second-organism delivered dosage meets or exceeds a predefined second-organism target dosage comprises:

detecting the second organism via a second-organism biochip device implanted in the second organism; and recalling the predefined second-organism target dosage in response to the second-organism biochip device.

11. The method of claim 9, wherein said terminating the second-organism duration of time when a calculated second-organism delivered dosage meets or exceeds a predefined second-organism target dosage comprises:

measuring a volume respirated by the second organism; and calculating the delivered dosage in response to the volume.

12. The method of claim 11, wherein said measuring a volume respirated by the second organism comprises:

measuring a volume of an animal restraint cartridge associated with a second-organism biochip device.

13. The method of claim 12, wherein said measuring a volume of an animal restraint cartridge associated with a second-organism biochip device comprises:

measuring a flow between an interior of the animal restraint cartridge and an exterior of the animal restraint cartridge.

14. A method comprising:

automatically conditioning an inhalent environment to achieve a predetermined environmental condition;

distributing to a first organism the conditioned inhalent environment for a first-organism duration of time;

distributing to a second organism the conditioned inhalent environment for a second-organism duration of time, distributing to a second organism includes coupling the inhalent environment to a second apertured connector containing at least a part of the second organism for the second-organism duration of time, coupling the inhalent environment to a second apertured connector includes opening a valve between the inhalent environment and the second apertured connector at a second-organism beginning time, and closing the valve between the inhalent environment and the second apertured connector at a second-organism ending time; and wherein the first organism and the second organism are exposed to the same conditioned inhalant environment after the inhalent environment has been completely conditioned.

15. A method comprising:

automatically conditioning an inhalent environment to achieve a predetermined environmental condition;

distributing to a first organism the conditioned inhalent environment for a first-organism duration of time;

distributing to a second organism the conditioned inhalent environment for a second-organism duration of time, distributing to a second organism includes coupling the inhalent environment to a second apertured connector containing at least a part of the second organism for the second-organism duration of time, coupling the inhalent environment to a second apertured connector includes closing a valve between a clean-air environment and the second apertured connector at a second-organism beginning time, and opening the valve between the clean-air environment and the second apertured connector at a second-organism ending time; and wherein the first organism and the second organism are exposed to the same conditioned inhalant environment after the inhalent environment has been completely conditioned.

16. A system comprising:

means for automatically conditioning an inhalent environment to achieve a predetermined environmental condition;

means for automatically distributing to a first organism the conditioned inhalent environment for a first-organism duration of time, said means for automatically distributing to a first organism includes means for coupling the inhalent environment to a first apertured connector, containing at least a part of the first organism, and disconnecting a clean-air supply to the first apertured connector for the first-organism duration of time; and means for automatically distributing to a second organism the conditioned inhalent environment for a second-organism duration of time; and wherein both distributing means provide exposure to the same conditioned inhalent environment after the predetermined environmental condition is achieved.

17. The system of claim 16, wherein said means for coupling the inhalent environment to a first apertured connector, containing at least a part of the first organism, for the first-organism duration of time comprises:

means for starting the first-organism duration of time upon an initial coupling of the inhalent environment to the first apertured connector containing the at least a part of the first organism; and means for terminating the first-organism delivered dosage when a calculated first-organism delivered dosage meets or exceeds a predefined first-organism target dosage.

18. The system of claim 17, wherein said means for terminating the first-organism duration of time when a calculated first-organism delivered dosage meets or exceeds a predefined first-organism target dosage comprises:
means for detecting the first organism via a first-organism biochip device implanted in the first organism; and
means for recalling the predefined first-organism target dosage in response to the first-organism biochip device.

19. The system of claim 17, wherein said means for terminating the first-organism duration of time when a calculated first-organism delivered dosage meets or exceeds a predefined first-organism target dosage comprises:
means for measuring a volume respirated by the first organism;
means for calculating the first-organism delivered dosage in response to the volume.

20. The system of claim 19, wherein said means for measuring a volume respirated by the first organism comprises:
means for measuring a volume of an animal restraint cartridge associated with a first-organism biochip device.

21. The system of claim 20, wherein said means for measuring a volume of an animal restraint cartridge associated with a first-organism biochip device comprises:
means for measuring a flow between an interior of the animal restraint cartridge and an exterior of the animal restraint cartridge.

22. The system of claim 16, wherein said means for coupling the inhalent environment to a first apertured connector, containing at least a part of the first organism, for the first-organism duration of time comprises:
means for opening a valve between the inhalent environment and the first apertured connector at a first-organism beginning time; and means for closing the valve between the inhalent environment and the first apertured connector at a first-organism ending time.

23. The system of claim 16, wherein said means for coupling the inhalent environment to a first apertured connector, containing at least a part of the first organism, for the first-organism duration of time comprises:

means for closing a valve between a clean-air environment and the first apertured connector at a first-organism beginning time; and means for opening a valve between the clean-air environment and the first apertured connector at a first-organism ending time.

24. A system comprising:

means for automatically conditioning an inhalent environment to achieve a predetermined environmental condition;

means for automatically distributing to a first organism the conditioned inhalent environment for a first-organism duration of time; and means for automatically distributing to a second organism the conditioned inhalent environment for a second-organism duration of time, said means for automatically distributing to a second organism includes means for coupling the inhalent environment to a second apertured connector containing at least a part of the second organism for the second-organism duration of time, said means for coupling the inhalent environment to a second apertured connector containing at least a part of the second organism for the second-organism duration of time includes means for starting the second-organism duration of time upon an initial coupling of the inhalent environment to the second apertured connector containing the at least a part of the second organism, and means for terminating the second-organism duration of time when a calculated second-organism delivered dosage meets or exceeds a predefined second-organism target dosage; and wherein both distributing means provide exposure to the same conditioned inhalent environment after the predetermined environmental condition is achieved.

25. The system of claim 24, wherein said means for terminating the second-organism duration of time when a calculated second-organism delivered dosage meets or exceeds a predefined second-organism target dosage comprises:

means for detecting the second organism via a second-organism biochip device implanted in the second organism; and means for recalling the predefined second-organism target dosage in response to the second-organism biochip device.

26. The system of claim 24, wherein said means for terminating the second-organism duration of time when a calculated second-organism delivered dosage meets or exceeds a predefined second-organism target dosage comprises:

means for measuring a volume respirated by the second organism; and means for calculating the delivered dosage in response to the volume.

27. The system of claim 26, wherein said means for measuring a volume respirated by the second organism comprises:

means for measuring a volume of an animal restraint cartridge associated with a second-organism biochip device.

28. The system of claim 27, wherein said means for measuring a volume of an animal restraint cartridge associated with a second-organism biochip device comprises:

means for measuring a flow between an interior of the animal restraint cartridge and an exterior of the animal restraint cartridge.

29. A system comprising:

means for automatically conditioning an inhalent environment to achieve a predetermined environmental condition;

means for automatically distributing to a first organism the conditioned inhalent environment for a first-organism duration of time; and means for automatically distributing to a second organism the conditioned inhalent environment for a second-organism duration of time, said means for automatically distributing to a second organism includes means for coupling the inhalent environment to a second apertured connector containing at least a part of the second organism for the second-organism duration of time, said means for coupling the inhalent environment to a second apertured connector containing at least a part of the second organism for the second-organism duration of time includes means for opening a valve between the inhalent environment and the second apertured connector at a second-organism beginning time, and means for closing the valve between the inhalent environment and the second apertured connector at a second-organism ending time; and wherein both distributing means provide exposure to the same conditioned inhalent environment after the predetermined environmental condition is achieved.

30. A system comprising:

means for automatically conditioning an inhalent environment to achieve a predetermined environmental condition;

means for automatically distributing to a first organism the conditioned inhalent environment for a first-organism duration of time; and means for automatically distributing to a second organism the conditioned inhalent environment for a second-organism duration of time, said means for automatically distributing to a second organism includes means for coupling the inhalent environment to a second apertured connector containing at least a part of the second organism for the second-organism duration of time, said means for coupling the inhalent environment to a second apertured connector containing at least a part of the second organism for the second-organism duration of time includes means for closing a valve between a clean-air environment and the second apertured connector at a second-organism beginning time, and means for opening the valve between the clean-air environment and the second apertured connector at a second-organism ending time; and wherein both distributing means provide exposure to the same conditioned inhalent environment after the predetermined environmental condition is achieved.

31. A method comprising:

automatically conditioning an inhalent environment to achieve a predetermined environmental condition;

distributing to a first organism the conditioned inhalent environment until a calculated first-organism delivered dosage meets or exceeds a predefined first-organism target dosage after the predetermined environmental condition has been achieved; and distributing to a second organism the conditioned inhalent environment until a calculated second-organism delivered dosage meets or exceeds a predefined second-organism target dosage after the predetermined environmental condition has been achieved.

32. The method of claim 31, wherein said automatically conditioning an inhalent environment comprises:

introducing an inhalent into an inhalent manifold.

33. The method of claim 32, wherein said introducing an inhalent into an inhalent manifold comprises:

introducing the inhalent into an inhalent intake plenum operably coupled with an inner manifold.

34. The method of claim 31, wherein said automatically conditioning an inhalent environment comprises:

monitoring at least one environmental condition selected from an environmental-condition group including temperature, relative humidity, pressure, and inhalent concentration.

35. The method of claim 31, wherein said automatically conditioning an inhalent environment comprises:

adjusting at least one environmental condition selected from an environmental-condition group including temperature, relative humidity, pressure, and inhalent concentration.

36. The method of claim 31, wherein said distributing to a first organism comprises:

detecting the first organism via a first-organism biochip device implanted in the first organism; and recalling the predefined first-organism target dosage in response to the first-organism biochip device.

37. The method of claim 31, wherein said distributing to a first organism comprises:

measuring a volume respirated by the first organism;

calculating the first-organism delivered dosage in response to the volume.

38. The method of claim 37, wherein said measuring a volume respirated by the first organism comprises:

measuring a volume of an animal restraint cartridge associated with a first-organism biochip device.

39. The method of claim 38, wherein said measuring a volume of an animal restraint cartridge associated with a first-organism biochip device comprises:

measuring a flow between an interior of the animal restraint cartridge and an exterior of the animal restraint cartridge.

40. The method of claim 31, wherein said distributing to a second organism comprises:

detecting the second organism via a second-organism biochip device implanted in the second organism; and recalling the predefined second-organism target dosage in response to the second-organism biochip device.

41. The method of claim 31, wherein said distributing to a second organism comprises:

measuring a volume respirated by the second organism; and calculating the delivered dosage in response to the volume.

42. The method of claim 41, wherein said measuring a volume respirated by the second organism comprises:

measuring a volume of an animal restraint cartridge associated with a second-organism biochip device.

43. The method of claim 42, wherein said measuring a volume of an animal restraint cartridge associated with a second-organism biochip device comprises:

measuring a flow between an interior of the animal restraint cartridge and an exterior of the animal restraint cartridge.

44. The method of claim 31, wherein said distributing to a first organism comprises:

coupling the inhalent environment to a first apertured connector containing at least a part of the first organism.

45. The method of claim 44, wherein said coupling the inhalent environment to a first apertured connector containing at least a part of the first organism comprises:

starting a first-organism duration of time upon an initial coupling of the inhalent environment to the first apertured connector containing the at least a part of the first organism; and terminating the first-organism duration of time when the calculated first-organism delivered dosage meets or exceeds the predefined first-organism target dosage.

46. The method of claim 44, wherein said coupling the inhalent environment to a first apertured connector containing at least a part of the first organism comprises:

opening a valve between the inhalent environment and the first apertured connector at a first-organism beginning time; and closing the valve between the inhalent environment and the first apertured connector at a first-organism ending time.

47. The method of claim 44, wherein said coupling the inhalent environment to a first apertured connector containing at least a part of the first organism comprises:

closing a valve between a clean-air environment and the first apertured connector at a first-organism beginning time; and opening the valve between the clean-air environment and the first apertured connector at a first-organism ending time.

48. The method of claim 31, wherein said distributing to a second organism comprises:

coupling the inhalent environment to a second apertured connector containing at least a part of the second organism.

49. The method of claim 48, wherein said coupling the inhalent environment to a second apertured connector containing at least a part of the second organism comprises:

starting a second-organism duration of time upon an initial coupling of the inhalent environment to the second apertured connector containing the at least a part of the second organism; and terminating the second-organism duration of time when the calculated second-organism delivered dosage meets or exceeds a predefined second-organism target dosage.

50. The method of claim 48, wherein said coupling the inhalent environment to a second apertured connector containing at least a part of the second organism comprises:

opening a valve between the inhalent environment and the second apertured connector at a second-organism beginning time; and closing a valve between the inhalent environment and the second apertured connector at a second-organism ending time.

51. The method of claim 48, wherein said coupling the inhalent environment to a second apertured connector containing at least a part of the second organism comprises:

closing a valve between a clean-air environment and the second apertured connector at a second-organism beginning time; and opening the valve between the clean-air environment and the second apertured connector at a second-organism ending time.

52. The method of claim 31, further comprising:

performing an inhalent or exposure study, wherein said performing the inhalent or exposure study comprises said automatically conditioning, said distributing to a first organism, and said distributing to a second organism.

53. A system comprising:

means for automatically conditioning an inhalent environment to reach a predetermined environmental condition;

means for automatically distributing to a first organism the conditioned inhalent environment until a calculated first-organism delivered dosage meets or exceeds a predefined first-organism target dosage after the predetermined environmental condition has been reached; and means for automatically distributing to a second organism the conditioned inhalent environment until a calculated second-organism delivered dosage meets or exceeds a predefined second-organism target dosage after the predetermined environmental condition has been reached.

54. The system of claim 53, wherein said means for automatically conditioning an inhalent environment comprises:

means for introducing an inhalent into an inhalent manifold.

55. The system of claim 54, wherein said means for introducing an inhalent into an inhalent manifold comprises:

means for introducing the inhalent into an inhalent intake plenum operably coupled with an inner manifold.

56. The system of claim 53, wherein said means for automatically conditioning an inhalent environment comprises:

means for monitoring at least one environmental condition selected from an environmental-condition group including temperature, relative humidity, pressure, and inhalent concentration.

57. The system of claim 53, wherein said means for automatically conditioning an inhalent environment comprises:

means for adjusting at least one environmental condition selected from an environmental-condition group including temperature, relative humidity, pressure, and inhalent concentration.

58. The system of claim 53, wherein said means for automatically distributing to a first organism comprises:

means for detecting the first organism via a first-organism biochip device implanted in the first organism; and means for recalling the predefined first-organism target dosage in response to the first-organism biochip device.

59. The system of claim 53, wherein said means for automatically distributing to a first organism comprises:

means for measuring a volume respirated by the first organism;

means for calculating the first-organism delivered dosage in response to the volume.

60. The system of claim 59, wherein said means for measuring a volume respirated by the first organism comprises:

means for measuring a volume of an animal restraint cartridge associated with a first-organism biochip device.

61. The system of claim 60, wherein said means for measuring a volume of an animal restraint cartridge associated with a first-organism biochip device comprises:

means for measuring a flow between an interior of the animal restraint cartridge and an exterior of the animal restraint cartridge.

62. The system of claim 53, wherein said means for automatically distributing to a second organism comprises:

means for detecting the second organism via a second-organism biochip device implanted in the second organism; and means for recalling the predefined second-organism target dosage in response to the second-organism biochip device.

63. The system of claim 53, wherein said means for automatically distributing to a second organism comprises:

means for measuring a volume respirated by the second organism; and means for calculating the delivered dosage in response to the volume.

64. The system of claim 63, wherein said means for measuring a volume respirated by the second organism comprises:

means for measuring a volume of an animal restraint cartridge associated with a second-organism biochip device.

65. The system of claim 64, wherein said means for measuring a volume of an animal restraint cartridge associated with a second-organism biochip device comprises:
means for measuring a flow between an interior of the animal restraint cartridge and an exterior of the animal restraint cartridge.

66. The system of claim 53, wherein said means for automatically distributing to a first organism comprises:
means for coupling the inhalent environment to a first apertured connector containing at least a part of the first organism.

67. The system of claim 66, wherein said means for coupling the inhalent environment to a first apertured connector containing at least a part of the first organism comprises:
means for starting a first-organism duration of time upon an initial coupling of the inhalent environment to the first apertured connector containing the at least a part of the first organism; and
means for terminating the first-organism duration of time when the calculated first-organism delivered dosage meets or exceeds the predefined first-organism target dosage.

68. The system of claim 66, wherein said means for coupling the inhalent environment to a first apertured connector containing at least a part of the first organism comprises:
means for opening a valve between the inhalent environment and the first apertured connector at a first-organism beginning time; and
means for closing the valve between the inhalent environment and the first apertured connector at a first-organism ending time.

69. The system of claim 66, wherein said means for coupling the inhalent environment to a first apertured connector containing at least a part of the first organism comprises:
means for closing a valve between a clean-air environment and the first apertured connector at a first-organism beginning time; and
means for opening the valve between the clean-air environment and the first apertured connector at a first-organism ending time.

70. The system of claim 53, wherein said means for automatically distributing to a second organism comprises:
means for coupling the inhalent environment to a second apertured connector containing at least a part of the second organism.

71. The system of claim 70, wherein said means for coupling the inhalent environment to a second apertured connector containing at least a part of the second organism comprises:
means for starting a second-organism duration of time upon an initial coupling of the inhalent environment to the second apertured connector containing the at least a part of the second organism; and
means for terminating the second-organism duration of time when the calculated second-organism delivered dosage meets or exceeds a predefined second-organism target dosage.

72. The system of claim 70, wherein said means for coupling the inhalent environment to a second apertured connector containing at least a part of the second organism comprises:
means for opening a valve between the inhalent environment and the second apertured connector at a second-organism beginning time; and
means for closing a valve between the inhalent environment and the second apertured connector at a second-organism ending time.

73. The system of claim 70, wherein said means for coupling the inhalent environment to a second apertured connector containing at least a part of the second organism comprises:
means for closing a valve between a clean-air environment and the second apertured connector at a second-organism beginning time; and
means for opening the valve between the clean-air environment and the second apertured connector at a second-organism ending time.

74. The system of claim 53, further comprising:
means for performing an inhalent or exposure study, wherein said means for performing the inhalent or exposure study comprises said means for automatically conditioning, said means for distributing to a first organism, and said means for distributing to a second organism.

75. A system comprising:
an inhalent manifold;
a clean-air manifold;
a first automatic independently-controllable exposure unit coupled to said inhalent manifold and said clean-air manifold;
a second automatic independently-controllable exposure unit coupled to said inhalent manifold and said clean-air manifold; and
an automatic exposure control system operably coupled to either or both said first exposure unit and said second exposure unit to provide an identical conditioned inhalent environment from said inhalent manifold to either or both said first exposure unit and said second exposure unit and to provide clean-air to either or both said first exposure unit and said second exposure unit during conditioning of the inhalent environment in said inhalent manifold.

76. The system of claim 75, wherein said inhalent manifold comprises:
an inhalent intake plenum operably coupled with an inner manifold.

77. The system of claim 75, wherein said inhalent manifold comprises:
at least one environmental-condition sensor integral with said inhalent manifold, said at least one environmental condition sensor selected from an environmental-condition-sensor group including a temperature sensor, a relative humidity sensor, a pressure sensor, and an inhalent concentration sensor; and
said exposure control system operably coupled to said at least one environmental-condition sensor.

78. The system of claim 75, wherein said inhalent manifold comprises:
at least one environmental-condition controller integral with said inhalent manifold, said at least one environmental-condition controller selected from an environmental-condition-controller group including a temperature controller, a relative humidity controller, a pressure controller, and an inhalent concentration controller; and
said exposure control system operably coupled to said at least one environmental-condition controller.

79. The system of claim 75, wherein said first independently-controllable exposure unit coupled to said inhalent manifold comprises:
an independently-controllable valve interposed between the inhalent manifold and a first apertured connector; and
said exposure control system operably coupled to said independently-controllable valve interposed between the inhalent manifold and a first apertured connector.

80. The system of claim 75, further comprising an exhaust manifold,
said first independently-controllable exposure unit coupled to said inhalent manifold comprises an independently-controllable valve interposed between the inhalent manifold and the exhaust manifold; and
said exposure control system operably coupled to said independently-controllable valve interposed between the inhalent manifold and the exhaust manifold.

81. The system of claim 75, wherein said first independently-controllable exposure unit coupled to said inhalent manifold comprises:
an animal restraint cartridge;
a biochip device receiver integral with said animal restraint cartridge; and
said exposure control system operably coupled to said a biochip device receiver.

82. The system of claim 75, wherein said first independently-controllable exposure unit coupled to said inhalent manifold comprises:
an animal restraint cartridge;
a differential volume sensor operably coupled to said animal restraint cartridge; and
said exposure control system operably coupled to said differential volume sensor.

83. The system of claim 82, wherein said differential volume sensor operably coupled to said animal restraint cartridge comprises:
a pneumotachograph operably coupled to said animal restraint cartridge; and
a differential pressure transducer operably coupled to said pneumotachograph.

84. The system of claim 75, wherein said second independently-controllable exposure unit coupled to said inhalent manifold comprises:
an independently-controllable valve interposed between the inhalent manifold and a second apertured connector; and
said exposure control system operably coupled to said independently-controllable valve interposed between the inhalent manifold and the second apertured connector.

85. The system of claim 75, further comprising an exhaust manifold,
said second independently-controllable exposure unit coupled to said inhalent manifold comprises an independently-controllable valve interposed between the inhalent manifold and the exhaust manifold; and
said exposure control system operably coupled to said independently-controllable valve interposed between the inhalent manifold and the exhaust manifold.

86. The system of claim 75, wherein said second independently-controllable exposure unit coupled to said inhalent manifold comprises:
an animal restraint cartridge;
a biochip device receiver integral with said animal restraint cartridge; and
said exposure control system operably coupled to said a biochip device receiver.

87. The system of claim 75, wherein said second independently-controllable exposure unit coupled to said inhalent manifold comprises:
an animal restraint cartridge;
a differential volume sensor operably coupled to said animal restraint cartridge; and
said exposure control system operably coupled to said differential volume sensor.

88. The system of claim 87, wherein said differential volume sensor operably coupled to said animal restraint cartridge comprises:
a pneumotachograph operably coupled to said animal restraint cartridge; and
a differential pressure transducer operably coupled to said pneumotachograph.

89. The system of claim 75, wherein said exposure control system comprises:
circuitry for
conditioning an inhalent environment in said inhalent manifold,
controlling said first independently-controllable exposure unit coupled to said inhalent manifold to expose at least a first organism to the inhalent environment for at least a first-organism duration of time, and
controlling said second independently-controllable exposure unit coupled to said inhalent manifold to expose at least a second organism to the inhalent environment for at least a second-organism duration of time; and
said circuitry selected from an electrical-circuitry group including electrical circuitry having at least one discrete electrical circuit, electrical circuitry having at least one integrated circuit, electrical circuitry having at least one application specific integrated circuit, electrical circuitry having a general purpose computing device configured by a computer program, electrical circuitry having a memory device, and electrical circuitry having a communications device.

90. The system of claim 89, wherein said circuitry comprises:
a data processing system running a control program.

91. A system comprising:
an inhalent manifold;
a clean-air manifold;
a first independently-controllable exposure unit coupled to said inhalent manifold;
a second independently-controllable exposure unit coupled to said inhalent manifold; and
an exposure control system operably coupled to either or both said first exposure unit and said second exposure unit, said exposure control system controls a period of connection between said inhalent manifold and either or both said first exposure unit and said second exposure unit after an inhalent environment in said inhalent manifold has reached a steady state, said exposure control system connects said clean-air manifold with any exposure unit that was exposed to inhalent at times other than the connection period.

92. The system of claim 91, wherein said inhalent manifold comprises:
an inhalent intake plenum operably coupled with an inner manifold.

93. The system of claim 91, wherein said inhalent manifold comprises:
- at least one environmental-condition sensor integral with said inhalent manifold, said at least one environmental condition sensor selected from an environmental-condition-sensor group including a temperature sensor, a relative humidity sensor, a pressure sensor, and an inhalent concentration sensor; and
- said exposure control system operably coupled to said at least one environmental-condition sensor.

94. The system of claim 91, wherein said inhalent manifold comprises:
- at least one environmental-condition controller integral with said inhalent manifold, said at least one environmental-condition controller selected from an environmental-condition-controller group including a temperature controller, a relative humidity controller, a pressure controller, and an inhalent concentration controller; and
- said exposure control system operably coupled to said at least one environmental-condition controller.

95. The system of claim 91, wherein said first independently-controllable exposure unit coupled to said inhalant manifold comprises:
- an independently-controllable valve interposed between the inhalent manifold and a first apertured connector; and
- said exposure control system operably coupled to said independently-controllable valve interposed between the inhalent manifold and a first apertured connector.

96. The system of claim 91, wherein said first independently-controllable exposure unit coupled to said inhalant manifold comprises:
- an independently-controllable valve interposed between the inhalent manifold and an exhaust manifold; and
- said exposure control system operably coupled to said independently-controllable valve interposed between the inhalent manifold and the exhaust manifold.

97. A system comprising:
- an inhalant manifold;
- a clean-air manifold;
- an exhaust manifold in communication with said inhalant manifold and said clean-air manifold;
- a plurality of independently controllable exposure units including a first valve and a second valve, each valve is operably connected to said inhalant manifold, said clean-air manifold and said exhaust manifold;
- during an inhalant exposure, said first valve is in open communication with said inhalant manifold and said exhaust manifold, and is in closed communication with said clean-air manifold; and
- during an inhalant exposure, said second valve is in open communication with said clean-air manifold and said exhaust manifold, and is in closed communication with said inhalant manifold.

98. The system of claim 97, wherein during a clean-air exposure,
- said first valve is in open communication with said clean-air manifold and said exhaust manifold, and is in closed communication with said inhalant manifold; and
- said second valve is in open communication with said inhalant manifold and said exhaust manifold, and is in closed communication with said clean-air manifold.

99. The system of claim 97, further comprising a controller in communication with and operating each first valve and second valve.

100. A system comprising:
- an inhalant manifold;
- a clean-air manifold;
- an exhaust manifold in communication with said inhalant manifold and said clean-air manifold;
- a plurality of independently controllable exposure units including a first valve and a second valve, each valve is operably connected to said inhalant manifold, said clean-air manifold and said exhaust manifold;
- a controller in communication with and operating each first valve and second valve.

101. A computer-readable medium having computer-executable instructions for performing the method steps recited in claim 9.

102. A computer-readable medium having computer-executable instructions for performing the method steps recited in claim 1.

103. A computer-readable medium having computer-executable instructions for performing the method steps recited in claim 31.

* * * * *